United States Patent
Masini

(10) Patent No.: US 6,267,785 B1
(45) Date of Patent: Jul. 31, 2001

(54) APPARATUS FOR POSITIONING A PROSTHETIC ELEMENT TO ACHIEVE A DESIRED ORIENTATION FOR CEMENTATION

(75) Inventor: Michael A. Masini, Ann Arbor, MI (US)

(73) Assignee: MedIdea, LLC, Ann Arbor, MI (US)

( * ) Notice: Subject to any disclaimer, the term of this patent is extended or adjusted under 35 U.S.C. 154(b) by 0 days.

(21) Appl. No.: 09/029,457
(22) PCT Filed: Jan. 31, 1997
(86) PCT No.: PCT/US97/01754
§ 371 Date: Mar. 5, 1998
§ 102(e) Date: Mar. 5, 1998
(87) PCT Pub. No.: WO97/27828
PCT Pub. Date: Aug. 7, 1997

(30) Foreign Application Priority Data

Feb. 1, 1996 (US) .................................................. 08/595277

(51) Int. Cl.$^7$ ...................................................... A61F 2/28
(52) U.S. Cl. .................... 623/23.22; 623/23.26; 623/22.12; 606/92
(58) Field of Search .......................... 606/92; 623/23.26, 623/23.27, 23.28, 23.22, 22.12

(56) References Cited

U.S. PATENT DOCUMENTS

| | | | |
|---|---|---|---|
| 3,067,740 | 12/1962 | Haboush ................. | 128/92 |
| 4,274,163 | 6/1981 | Malcom et al. ......... | 3/1.91 |
| 4,337,773 | 7/1982 | Raftopoulos et al. ... | 128/305 |
| 4,357,716 * | 11/1982 | Brown ..................... | 606/92 |
| 4,404,692 * | 9/1983 | Eftekhar ................. | 606/92 |
| 4,686,973 | 8/1987 | Frisch ..................... | 128/92 |
| 4,697,584 | 10/1987 | Haynes ................... | 128/92 |
| 4,815,454 | 3/1989 | Dozier, Jr. .............. | 128/92 |
| 4,896,662 | 1/1990 | Noble ...................... | 606/94 |
| 4,983,183 | 1/1991 | Horowitz ................. | 623/23 |
| 4,994,085 | 2/1991 | Sawai et al. ............ | 623/23 |
| 5,047,061 * | 9/1991 | Brown ..................... | 606/92 |
| 5,078,746 * | 1/1992 | Garner ................... | 623/23.26 |
| 5,340,362 | 8/1994 | Carbone ................. | 623/23 |
| 5,501,687 | 3/1996 | Willert et al. .......... | 606/94 |
| 5,746,771 * | 5/1998 | Clement, Jr. et al. .. | 623/23.22 |
| 5,766,262 * | 6/1998 | Mikhail .................. | 623/23.26 |
| 6,010,535 * | 1/2000 | Shah ...................... | 623/23.23 |

* cited by examiner

Primary Examiner—David H. Willse
Assistant Examiner—Suzette J. Jackson
(74) Attorney, Agent, or Firm—Gifford, Krass, Groh, Sprinkle, Anderson & Citkowski, PC

(57) ABSTRACT

Apparatus and method are disclosed for maintaining the proper positioning of an implant (310, 504) within a prepared bone cavity (312) during cement injection and curing. First stabilization means (340, 480), implantable within the bone cavity, minimize lateral movement of the implant distal end, while second stabilization means (330, 334, 406, 404), physically separate from the first stabilization means (340, 480), minimize both the lateral movement of the implant proximal end and the rotational movement of the implant overall. In the preferred embodiment, the second stabilization means (330, 334) includes an aperture cap (334) removable securable to the end of a prepared bone. This cap (334), preferably further includes first and second ports (322, 336) associated, respectively, with cement injection and cement over-pressurization. In an alterative embodiment, the second stabilization means (406, 404) includes a manually operated mechanism enabling (404) the implant (504) to be temporarily, yet rigidly, secured thereto in accordance with a desired orientation, preferably affording adjustments along multiple degrees of freedom prior to the rigid securement thereof.

24 Claims, 5 Drawing Sheets

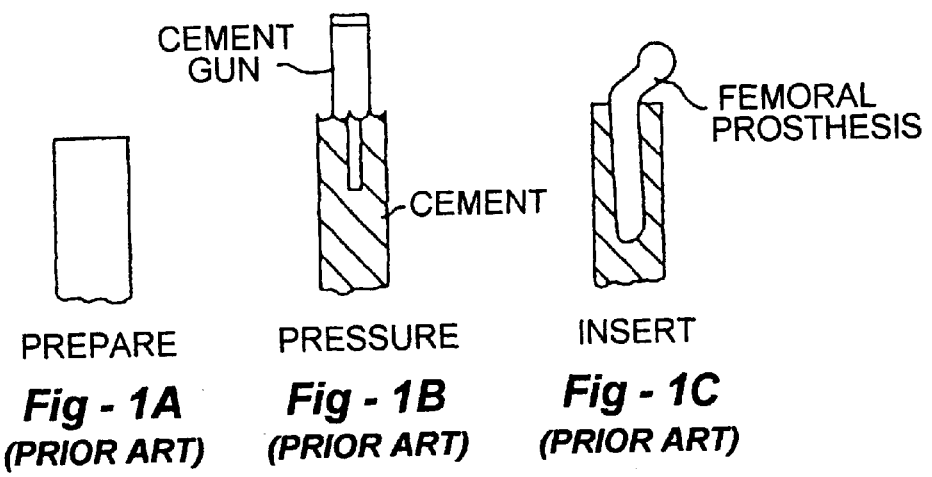
Fig - 1A (PRIOR ART)
Fig - 1B (PRIOR ART)
Fig - 1C (PRIOR ART)
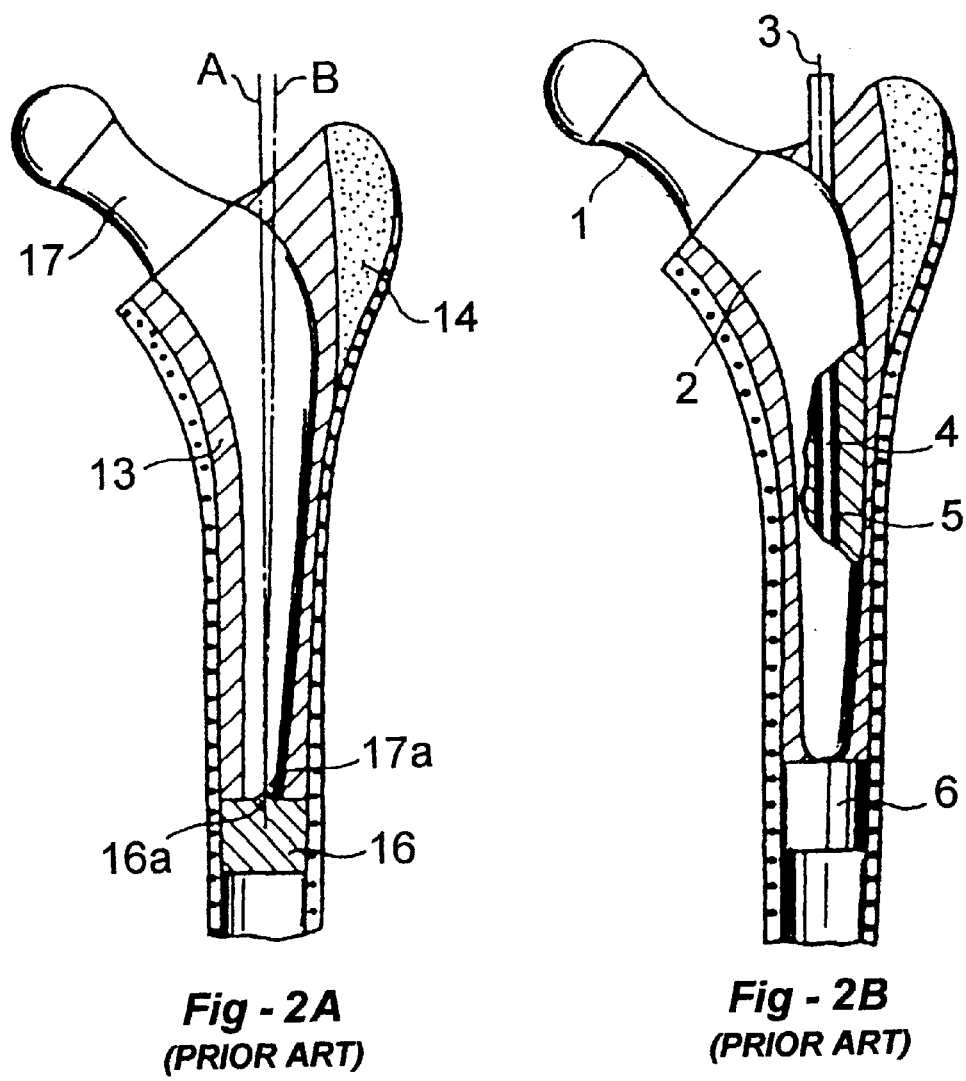
Fig - 2A (PRIOR ART)
Fig - 2B (PRIOR ART)

APPARATUS FOR POSITIONING A PROSTHETIC ELEMENT TO ACHIEVE A DESIRED ORIENTATION FOR CEMENTATION

This application corresponds to the U.S. national phase of Patent Cooperation Treaty application No. US97/01754, filed Jan. 31, 1997 under 35 U.S.C. §371, which claims priority of U.S. patent application Ser. No. 08/595,277, filed Feb. 1, 1996 now abandoned, the entire contents of both of which are incorporated herein by reference.

FIELD OF THE INVENTION

This invention relates generally to arthroplasty and, more particularly to devices and techniques for positioning a prosthesis prior to fixation through the injection of a bonding agent.

BACKGROUND OF THE INVENTION

In current human joint repair situations, it is common practice to prepare host bone stock to receive an implant then, if satisfied with the physical correspondence, apply cement to the host, install the prosthesis, and stabilize the arrangement until curing. This approach has several disadvantages. Foremost among them arises from the unpredictable process of ensuring that, although the prosthesis may have been ideally placed prior to cementation, once the cement is applied, orientation may shift, resulting in a final configuration which is less than optimal.

A few approaches have been attempted to assist in making the positioning of the final implant more predictable. As discussed further in the detailed description herein, one such approach utilizes a centralizing plug inserted distally within the medullary canal, and from which there extends a rod upon which a final implant including a corresponding central bore may be monorailed. The plug and rod are positioned in conjunction with a trial which also includes a central bore, which is then removed, the intramedullary cavity filled with cement and the final implant slid over the rod, displacing the cement as it is pushed down into position. Although this technique may assist in maintaining a side-to-side orientation prior to cementation, it does not address the simultaneous need for up-and-down and/or rotational stabilization. Additionally, as with current techniques, cement is applied to the host prior to the introduction of the final implant, leaving open the possibility that the final implant may be held in a position different from that associated with the trial, and may therefore result in an unacceptable misplacement as the cement cures.

Other approaches do reverse this order, and install the final implant prior to the injection of cement. The known approaches, however, utilize a highly specialized prosthetic device including centralizing protrusions and internal channels through which the cement is introduced. That is, in these systems, the prosthesis itself is used as the cement injector. Due to their requirement for a highly specialized final prosthetic element, such systems are incompatible with currently available implant devices, and therefore raise costs while reducing the options of the practitioner. In addition, they do not adequately address the need for simultaneously stabilizing multiple degrees of freedom prior and during cementation. As a further disadvantage, the systems which use the prosthesis as the cement injector tend to use the cement as a grout between the outer surface of the implant and the inner surface of the receiving cavity. It has been shown, however, that the changes of success are improved through the creation of a thicker cement "mantle," as opposed to a thin grout-type layer. The need remains, then, for a system whereby the prosthesis may be stabilized relative to multiple degrees of freedom prior to cementation, and, ideally, remain compatible with existing prosthetic components while forming a strong and stable bond to the host.

SUMMARY OF THE INVENTION

The present invention resides in apparatus and methods for maintaining the proper positioning of a prosthetic implant having proximal and distal ends within a prepared bone cavity during cement injection and curing. In contrast to prior-art systems the invention provides first stabilization means, implantable within the bone cavity, for minimizing lateral movement of the distal end of the implant, and second stabilization means, physically separate from the means for minimizing lateral movement of the distal end of the implant, for minimizing both the lateral movement of the proximal end of the implant and the rotational movement of the implant overall. In the preferred embodiment, the second stabilization means includes an apertured cap removably securable to the end of a bone having the prepared cavity through which the implant is inserted and held in place. This cap, which may either be entirely rigid or include a pliable membrane in the vicinity of the aperture, preferably further includes a first port associated with cement injection and a second port associated with cement over-pressurization. In an alternative embodiment, the second stabilization means includes a manually operated mechanism enabling the implant to be temporarily yet rigidly secured thereto in accordance with a desired orientation, preferably affording adjustments along multiple degrees of freedom prior to the rigid securement thereof.

BRIEF DESCRIPTION OF THE DRAWINGS

FIG. 1A illustrates, in skeletal form, the first step of a prior-art implantation sequence involving host bed preparation;

FIG. 1B depicts an intermediate step in the prior-art sequence wherein the cavity prepared according to FIG. 1A is filled with cement;

FIG. 1C illustrates the final phase of this prior-art sequence wherein a femoral prosthesis is inserted into the injected cement prior to hardening;

FIG. 2A illustrates a prior-art improvement over the sequence shown in FIGS. 1A through 1C, wherein a distal plug is used for distal centering of the implant;

FIG. 2B illustrates yet another prior-art improvement over the approach of FIG. 2A wherein a vertically oriented rod is attached to the distal plug over which an implant may be slid after cement injection to further inhibit movement during curing;

DETAILED DESCRIPTION OF THE PREFERRED EMBODIMENTS

FIG. 1 of U.S. Pat. No. 5,340,362 shows an existing, prior-art procedure for inserting and cementing a prosthesis into a bone cavity, and this figure has been reproduced herein. In accordance with this technique, the canal is reamed or broached as shown in FIG. 1A, and a trial is typically inserted thereinto to ensure that the final prosthetic component will be properly received. After this trialing, cement is injected into the excavated area as shown in FIG. 1B, and the prosthesis is inserted as shown in FIG. 1C, and left in position while the cement hardens. As discussed in the background of the instant invention, the technique just described is deficient in that, although the prosthesis may be optimally oriented during the trial procedure, the position of the actual implant may shift upon insertion into the cemented host or thereafter, resulting in a misaligned final fixation.

Figure 4:
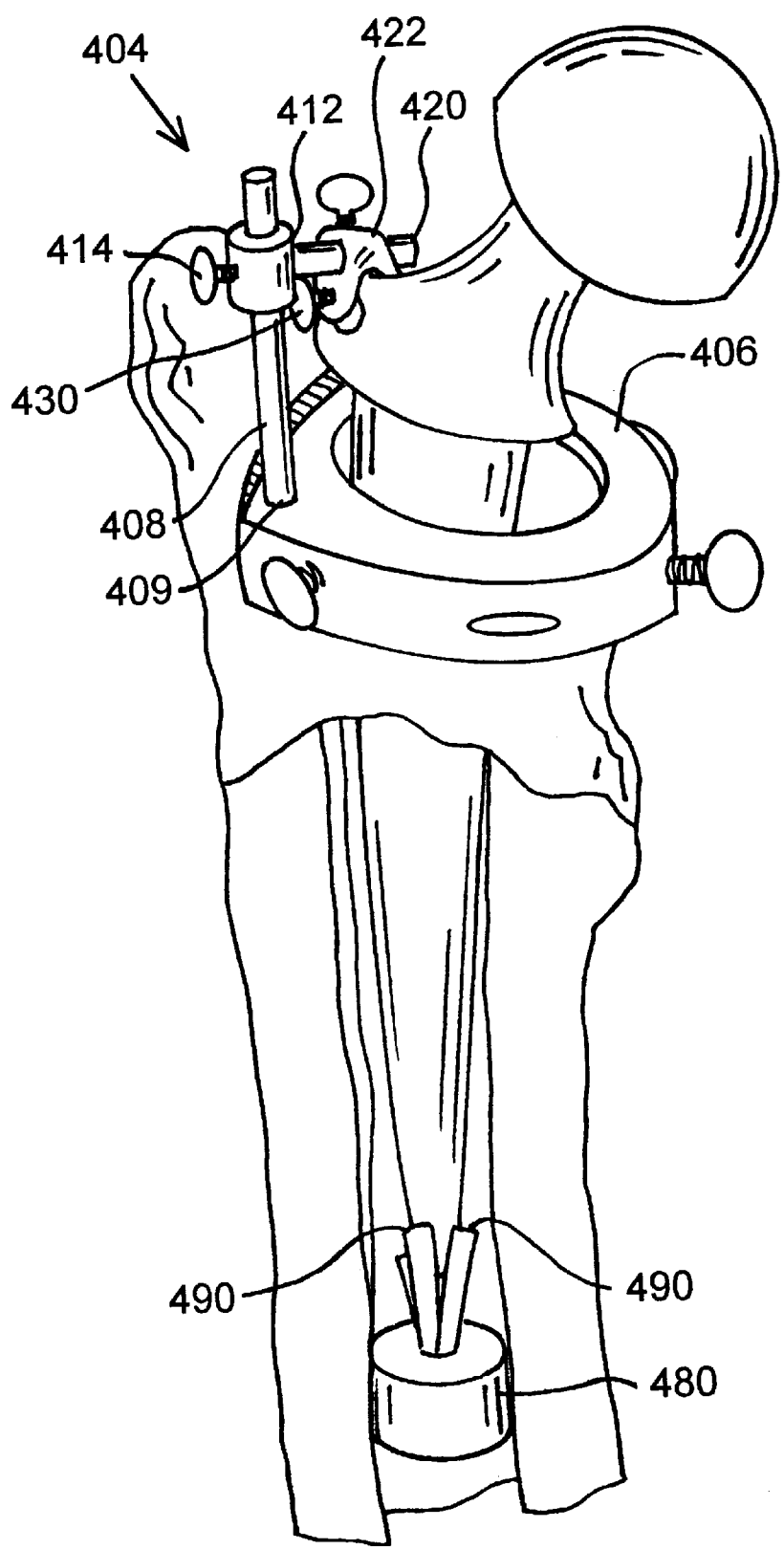
FIG. 4 illustrates two independently usable alternative embodiments according to the invention, including a multiple degree-of-freedom proximal retainment structure and a distal plug including leaf springs.
Figure 6:
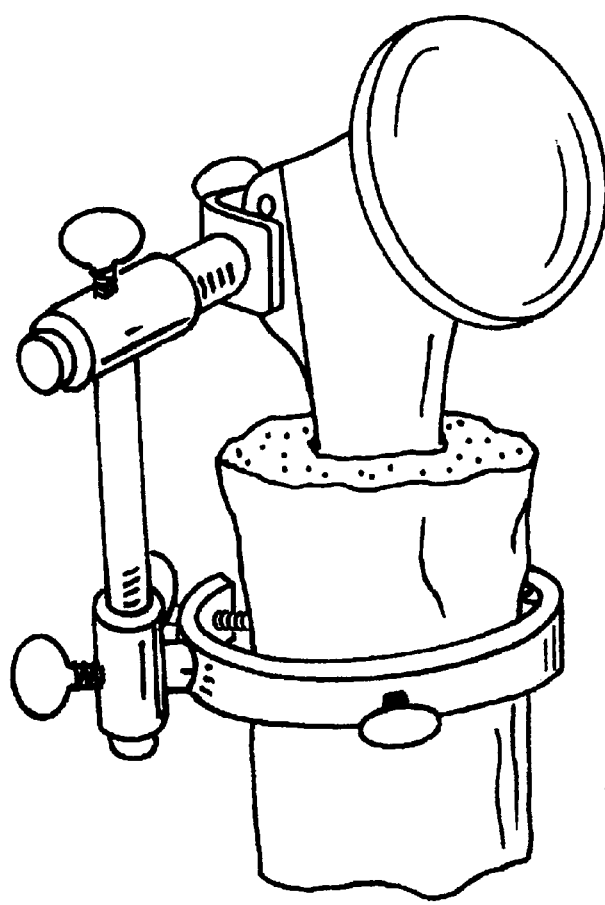
FIG. 6 is a drawing which shows how the invention could be applied to a humeral prosthesis.

Various improvements also exist in the prior art to minimize such adjustment problems. At the very least, as shown in FIG. 6 of U.S. Pat. No. 4,994,085, reproduced herein as FIG. 2A, a distal centralizer 16 is inserted beforehand into the intramedullary cavity 13 to which the distal tip 17a of the implant 17 engages at point 16a. This, at least, stabilizes the relative position of the distal tip 17a, resulting in a narrower range of angles (A to B) through which the implant 17 may move within the cement-filled cavity prior to final curing. The teachings of this reference further improve upon post-cementation stabilization by incorporating a stabilizing rod 4 into the distal plug 6 over which a specially designed implant 2 having a centralized hole 4 is slidably installed, as shown in FIG. 2B herein (FIG. 4 of the issued patent). Assuming the various connections between rod 5, plug 6 and the inner walls of the intermedullary canal are relatively rigid, and the various tolerances involved are substantially tight, movement of the implant 2 is further restricted until the cement finally cures.

Another approach taken according to the prior art involves the injection of cement after positioning of a specially designed implant into a prepared cavity. The '362 patent referenced above is directed toward such an approach. As with other arrangements of type, the final implant includes a cement canal along its longitudinal axis. A bone-cement injector is threaded onto the proximal portion of this cement canal, causing the cement to subsequently travel down and through the implant, eventually exiting through openings in and around its distal tip. A restrictor plug halts downward cement travel, thus initiating an upward, retrograde filling of the void in between the prosthesis and the cancellous bone wall. In addition to a single distal aperture through which the injected cement is introduced, side ports may also be included, as shown in U.S. Pat. No. 4,274,163 and various other prior-art references.

The methods and associated apparatus just described exhibit various shortcomings. In the technique described with reference to FIG. 2B herein, although movements within the curing cement bed are further restricted, the point of substantial stability remains at the distal tip of the implant, enabling a certain level of proximal misalignment to continue, as no true proximal stabilization is provided. Worse, perhaps, is that since the centering rod and bore through the specialized component are both circular, the final implant is still subject to up-and-down and/or rotational variation, resulting in potential misalignment upon fixation.

With respect to the techniques wherein cement is injected after installation, although the implant may be stabilized both proximally and distally as the cement is injected, as with the device of the '085 patent, a specially designed implant including the injector ports must be utilized, resulting in a specialized unit demanding significantly higher cost. Furthermore, regardless of the existing system utilized, attention to the pressure of the cement during injection and curing has not been adequately addressed. Although, for example, the system described in the '163 patent referenced above utilizes various components to maintain pressurization, numerous sophisticated articles are required, including a high pressure nitrogen gas source, disposable cylinder and various associated valves and tubing which may be difficult to assemble, require skilled operators, or create expensive waste and maintenance problems.

The present invention improves upon the prior art by providing a simplified apparatus and associated installation methods whereby an implant may be oriented both proximally and distally prior to the injection of cement, while, at the same time, providing means for guarding against rotational and up/down movement of the implant as well during such injection and subsequent curing. In addition, configurations according to the invention provide a simple means for expelling over-pressurized cement, thereby yielding a simple, but satisfactory indication that sufficient cement has been injected to an acceptable level. Although, in one embodiment, the invention makes advantageous use of a longitudinal bore through the implant, in another embodiment, all of the above improvements and advantages are realized in conjunction with standard, currently available prostheses, thus resulting in an approach which is both straightforward and economical.

Figure 3:
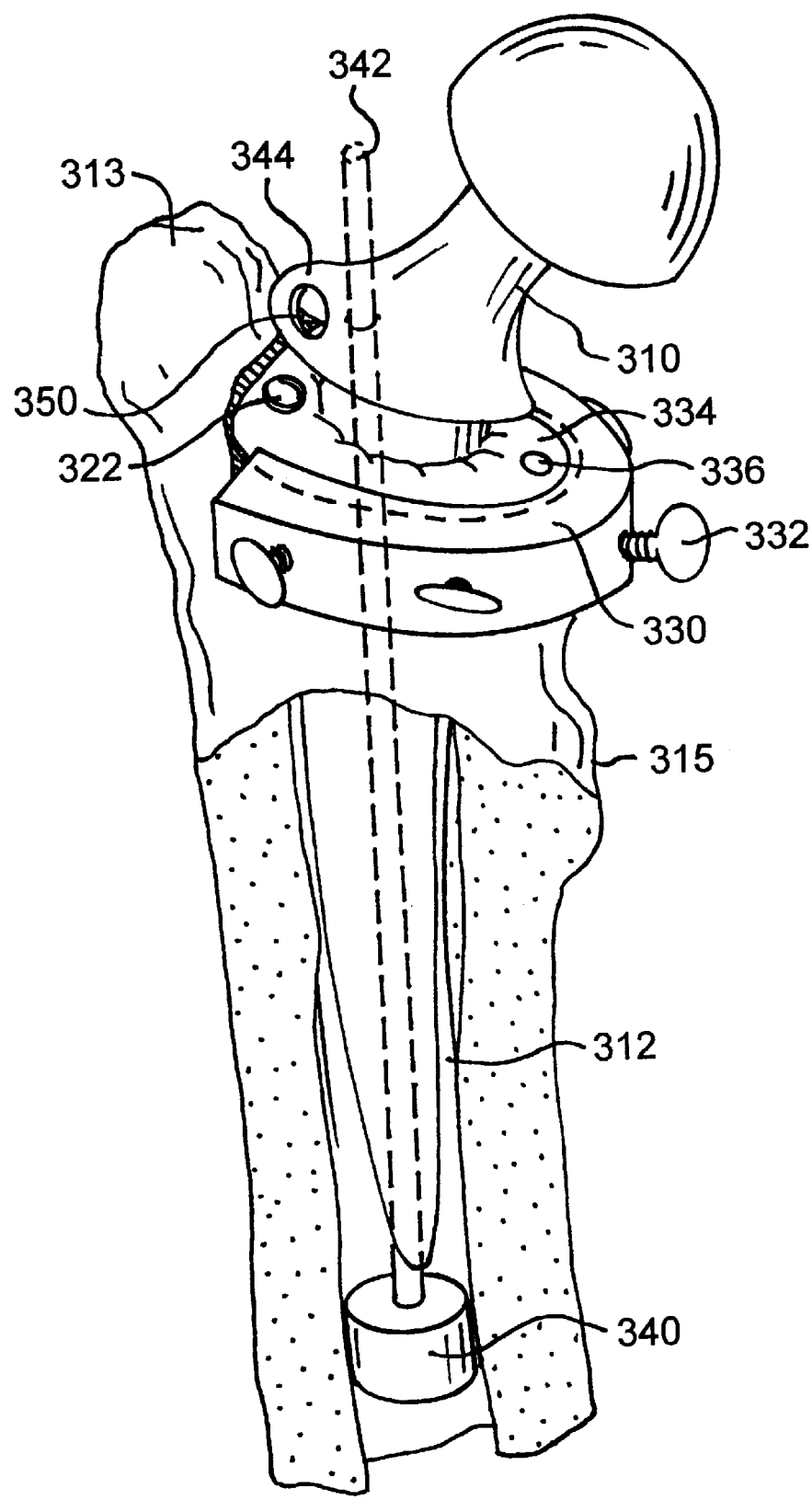
FIG. 3 is an arrangement according to this invention showing the use of a proximal cap which may be used either with a specially prepared prosthetic device or commercially available unit.
Figure 7:
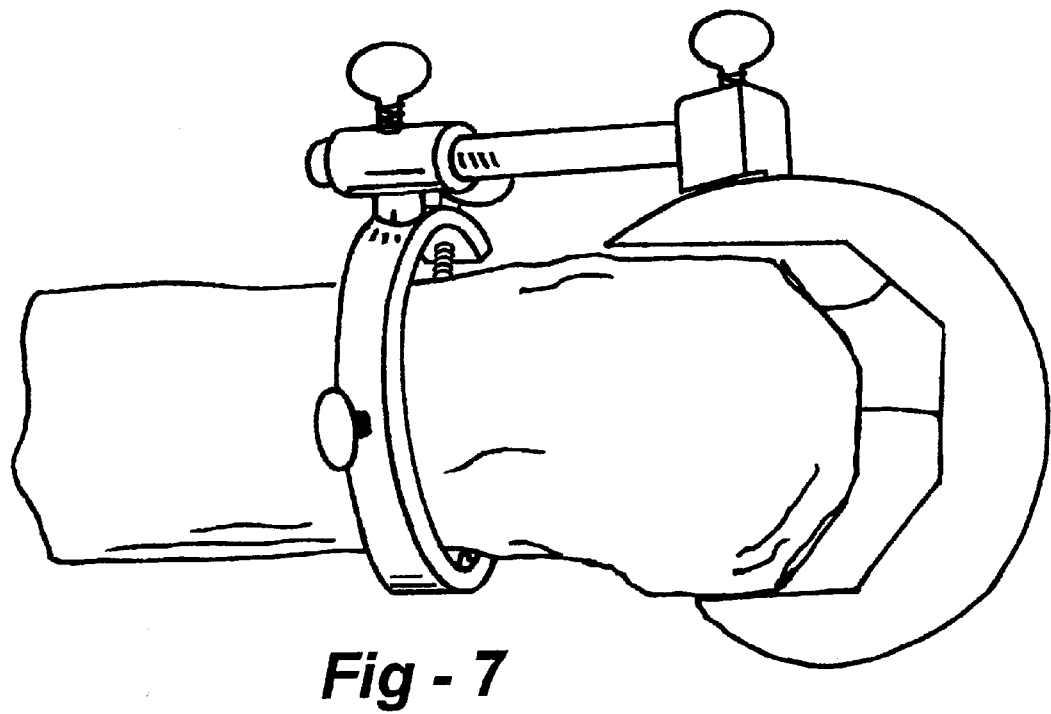
FIG. 7 is a drawing which shows how the invention may be applied to knee arthroplasty.

FIG. 3 is an oblique drawing of an arrangement according to this invention depicting various independent embodiments. Overall, an implant 310 is shown inserted into a prepared cavity 312, in this case the implant 310 being a femoral hip prosthesis and the cavity 312 being the intramedullary canal, though, as will be apparent to those of skill in the art of orthopaedics, the general principles disclosed herein are not restricted to this application, and may be used in other joint situations, including the knee (FIG. 7), shoulder (FIG. 8) and other situations. Certain features of the femur are shown such as the greater trochanter 313 and lesser trochanter 315, and it is assumed that a resection not visible in this figure has been performed on at least a portion of the proximal end of the femur along with reaming and other preparation of the medullary canal itself to accept the implant 310.

Broadly, according to the invention, an apertured proximal sealing cap is installed over the resection portion of the femoral shaft, the prosthesis 310 is inserted through the proximal opening 320 of the seal, and cement is injected through an injection port 322. In a preferred embodiment, this proximal seal includes a horseshoe-shaped collar 330 having one or more means such as thumb screws 332 for releasably securing the collar 330 over the bone, and a preferably pliable gasket 334 made from rubber or other suitable polymeric materials through which the aperture 320 is formed. Also located on and through this gasket 334 is a flap valve 336 wherein the material forming the gasket 334 is adjusted to flap open or rupture at a predetermined pressure level, preferably on the order of 25 mm of mercury, which has shown to be advantageous for such orthopaedic purposes. Preferably, this flap valve 336 is formed either by scoring the material of the gasket 334 in a manner conducive to such rupture, or, alternatively, the material may be thinned in this area to break under load.

The embodiment of the proximal seal just described is that preferred for use in conjunction with standard, commercially available implants. That is, the aperture 320 formed in the gasket 334 may take the form of a slit, an oval, or another shape appropriate to the stem of the implant, enabling the device to be inserted therethrough and retained in place by the surrounding material of the gasket 334 against the stem, either through friction or high-tolerance. Alternatively, then, if a more precise geometry of the stem at the point where it emerges through the proximal seal is known, the material 334 may be of a more rigid composition, and may, in fact, be integrally formed to the collar 330, in which case the injection port 322 and valve 336 may be more elaborate and substantial. For example, if the area 334 is metal, the port 322 may be threaded for a more solid connection to commercially available injector nozzles, and the valve 336 may take advantage of more sophisticated pressure-release techniques available in the art, including adjustability for a particular pressure or range of pressures.

Whether the implant is of a standard configuration or specialized for use in conjunction with the invention, a distal spacer 340 is preferably utilized for distal centering. A longitudinal rod 342 may optionally be added to, or installed on the plug 340, requiring a specialized implant having a longitudinal bore 344 akin to that described in the '085 patent referred to above, the exception being that, according to this invention, the implant 310 would be monorailed onto the optional rod 342 prior to the injection of cement into the cavity formed between the walls of the implant and the prepared medullary canal. Thus, as discussed above, the present invention may either be used with a specially prepared implant having this longitudinal bore and/or convenient wall geometries or, alternatively, and unlike the prior art, a standard prosthesis may be used.

In the event that the prosthesis includes an arrangement to assist in installation or removal such as ring 350, the alternative proximal stabilization configuration of FIG. 4 may be used. To further assist in proximal securement, a multiple degree-of-freedom clamp arrangement illustrated generally at 404 may be attached to a proximal cover 406 secured to femoral end or attached to a portion of available bone material by whatever means. In the embodiment shown, a first rod 408 securely affixed to the member 406 at point 409, onto which there is disposed a slidable collar 412 which may be locked into position with a suitable device such as thumb screw 414. A second rod 420 and collar 422 contains two thumb screws, one to lock the collar 422 in position along rod 420, and a different thumb screw 430 for positive engagement with the prosthesis proper. It will be understood to those of skill that various other approaches may be utilized in accordance with the general principle contained herein to grasp and hold any portion or aperture of a standard implant without requiring its modification.

FIG. 4 also shows an alternative distal plug according to the invention which may be used in combination with any of the embodiments previously described. With such an inventive plug, it is first seated distally at an appropriate distance within the intermedullary canal, and includes a plurality of deformable upwardly oriented leaf springs 490. Accordingly, with the plug 480 installed in place as shown, an even more generalized type of implant, and not requiring an actual, solid connection to such a distal spacer, may be inserted down and into the medullary canal and held in place while resisting distal side-to-side motion as the distal tip of the implant is retained within these leaf springs 490. This also allows adjustments in a longitudinal direction enabling fine tuning at the effective length of the implant. Note in FIG. 4 that the aperture through which the implant is inserted is quite a bit larger than that shown in FIG. 4 and, in fact, does not include a seal per se. This is due to the fact that, in accordance with this embodiment, cement may, in fact, be injected prior to or after the implant is held in place both proximally and distally. Indeed, according to this particular embodiment, a standard distal plug may be used in conjunction with the mechanism shown generally at 404 even without a cap or collar as shown. For example, this mechanism 404 may simply attach to an existing bone surface or structure instead of the point 409, thereby holding the implant in place proximally and distally while preventing motion in all dimensions as the cement cures, regardless of when it was injected. In accordance with an alternative methodology, the proximal and distal stabilizers may be used in conjunction with a trial then, upon achieving a desired orientation, a single manual fastener may be loosened, and the actual implant installed in the exact configuration of the trial to guarantee proper positioning.

Figure 5:
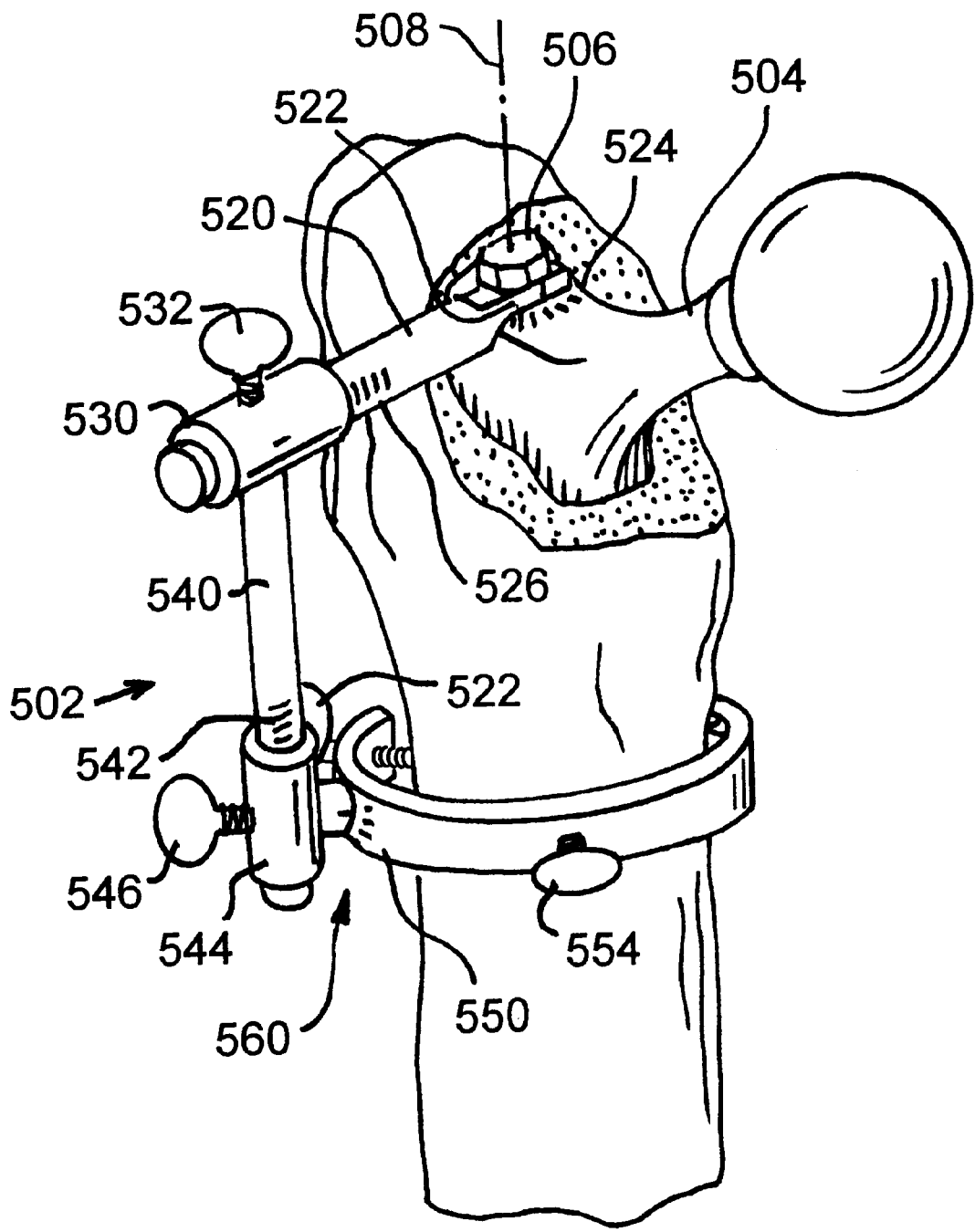
FIG. 5 is a drawing which shows, from an oblique perspective, an alternative embodiment of the invention which clamps around the femur below the area of resection, and attaches to an elongated fastener oriented generally lengthwise with respect to the implant.

FIG. 5 illustrates an alternative embodiment of the invention, seen generally at 502 from an oblique perspective. In this case, a prosthesis 504, which may have a threaded bore along an axis 508 to receive a threaded fastener such as a bolt 506, is physically coupled to a first structural element 520 which slidably engages with a collar 530, and which may be tightened in place with a manual fastener such as thumb screw 532. Other types of fasteners, including those requiring tools such as set screws, may alternatively be utilized for this purpose. In this embodiment, the prosthesis 504 may be rotated about the axis 508 with the bolt 506 in a slightly loosened condition, and then tightened when a desired angular rotation is achieved. A score mark 522 may be used in conjunction with score marks 524 to provide an indication of this desired angular rotation for future reference. Preferably, score marks are provided on the underside of member 520 as well in the vicinity of the attachment to the prosthesis, to assist in maintaining the desired rotational configuration once the bolt 506 is tightened. Prosthetic devices having a threaded bore along axis 508 are available from the Zimmer Company, though in the event that such a feature is not provided for, connection may be made to the prosthetic element itself as disclosed elsewhere herein, rendering this threaded bore convenient but not necessary to the invention.

Preferably in this embodiment a set of score marks 526 are also provided on the member 520, such that with the member 520 being moved back and forth to adjust the lateral or transverse positioning of the implant, the fastener 532 may be used to lock the configuration in place, with the marks 526 being used to maintain a visual indication of the desired lateral configuration. Attached to collar 530 is a downwardly extending member 540, which is received by a collar 544 having a manual adjustment device 546. The member 540 may also include markings 542, such that, as the element 540 is moved up and down to adjust for the axial length of the prosthesis, fastener 546 may be locked with the score marks 542 providing a visual indication.

The collar 544 is attached to a clamp 550, which is rigidly attached to the outer surface of the femur through manual fasteners 552 and 554. As a further optional convenience, the collar 544 may be rotationally variable, and locked into place along with member 540 with manual fastener 546, with optional score marks 560 being used as a visual indication of this configuration, if so desired.

Although the various embodiments of this invention may be used to properly position a trial implant prior to the positioning of a final prosthetic element, it should be apparent that in all cases, the device such as 504 in FIG. 5 is assumed to be the final implant itself, thereby eliminating the need for a trial. Particularly if the various positioning elements of the invention are sufficiently low in profile, the entire assembly, including those shown in the figures, joint reduction may be carried out, with the various fasteners being adjustably and rigidly clamped, with the final implant positioned in place and rigidly connected thereto. Following this procedure, the properly positioned implant may be removed from its reduced configuration and cemented. According to the invention, depending upon the circumstances, the prosthesis may be cemented in situ, with the various positioning members according to the invention remaining locked in place, or, alternatively, one or more of the fasteners may be loosened, with the implant and, perhaps, other fasteners attached thereto, removed and repositioned once cement has been injected into the intramedullary canal.

For example, referring to the embodiment of FIG. 5, fastener 546 may be slightly loosened, with the prosthesis 504 and members 520 and 540 rigidly attached thereto being temporarily removed, the cavity filled with cement, and the prosthesis with members 520 and 540 reinserted, with member 540 being reinstalled into collar 544, utilizing the score marks 542 to ensure that fixation will take place at a proper and desired orientation upon re-tightening of the fastener 546. It will also be apparent that in the embodiment of FIG. 5 and others disclosed herein, that if the assembly attached to the femur and to the prosthetic element through using one or more structural elements according to the invention is sufficiently rigid, positioning of the final implant may be stabilized in three dimensions (for example, rotationally, transversely, and axially—i.e., with respect to the coronal, sagittal and transverse planes).

Having thus described my invention, what is claimed is:

1. Apparatus for positioning a prosthetic element having an outer convex articulating surface configured to interact with a corresponding concave joint surface to achieve a desired orientation relative to a bone, the apparatus comprising:
    a removable mechanism for temporarily attaching the prosthetic element to the bone, such that the outer convex articulating surface of the prosthetic element remains exposed when attached to permit articulation with the corresponding concave joint surface as part of a trial joint reduction, the removable mechanism including one or more fasteners for:
    a) adjusting the positioning of the prosthetic element in one or more dimensions, and
    b) rigidly looking the prosthetic element into place once the desired orientation is achieved in accordance with the interaction between the outer convex articulating surface of the prosthetic element and the corresponding concave joint surface.

2. The apparatus of claim 1, wherein the bone is a femur or humerus, and the prosthetic element is an intramedullary trial or final implant.

3. The apparatus of claim 2, further including a device to center the implant within the intramedullary canal.

4. The apparatus of claim 1, wherein the mechanism includes a plurality of structural elements and fasteners enabling the prosthetic element to be adjusted rotationally, transversely and axially in order to achieve the desired orientation.

5. The apparatus of claim 1, wherein the mechanism includes an elongated structural element having one end attached to the device and a second structural element having one end attached to the prosthetic element, and the other ends of both structural elements being adjustably and lockingly connected to one another.

6. Apparatus for establishing the proper positioning of a humeral or femoral implant within an intramedullary canal of a bone, the implant having an outer convex articulating surface configured to interact with a corresponding concave joint surface, the apparatus comprising:
    a collar which removably surrounds at least a portion of the bone for rigid temporary attachment thereto:
    at least one structural element for rigidly coupling the collar to the implant such that the outer convex articulating surface of the implant remains exposed to permit articulation with the corresponding concave joint surface as part of a trial joint reduction,
    the structural element including one or more fasteners which may be loosened to adjust the orientation of the prosthetic element relative to the bone, then tightened once the desired orientation is achieved in accordance with the interaction between the outer convex articulating surface of the implant and the corresponding concave joint surface.

7. The apparatus of claiim 1, wherein the mechanism includes:
    a collar which surrounds at least a portion of the bone; and
    one or more fasteners which engage with an outer surface of the bone to hold the collar in place.

8. The apparatus of claim 7, wherein the mechanism includes a first structural element having one end attached to the bone and a second structural element having one end attached to the prosthetic implant, the other ends of both structural elements being adjustably and lockingly connected to one another.

9. The apparatus of claim 6, including a plurality of structural elements enabling the implant to be adjusted rotationally, laterally, and in terms of length in order to achieve the desired orientation.

10. The apparatus of claim 6, further including an intramedullary plug engageable with the distal end of the implant.

11. The apparatus of claim 10, wherein the plug includes a plurality of upwardly oriented leaf springs configured to engage with the distal end of the implant.

12. A method of positioning a trial or final prosthetic element having an outer convex articulating surface configured to interact with a corresponding concave joint surface relative to a bone so as to achieve a desired orientation, the method comprising the steps of:
    attaching an adjustable, lockable structural assembly to the bone, the assembly having an end adapted for attachment to the prosthetic element;
    reducing the bone with the assembly attached into a joint so as to test the interaction between the outer convex articulating surface of the element and the corresponding concave joint surface;
    adjusting the position of the prosthetic element in one or more dimensions so as to achieve the desired orientation; and
    locking the prosthetic element into place once the desired orientation is achieved.

13. The method of claim 12, wherein the bone is a femur or humerus and the prosthetic element is an intramedullary implant.

14. The method of claim 12, wherein the steps of adjusting the orientation of the prosthetic element and locking the prosthetic element into position are both performed as part of the trial joint reduction.

15. Apparatus for positioning a trial or final prosthetic element relative to a bone so as to achieve a desired orientation, comprising:

a device which rigidly and removably attaches to the bone;

a removable mechanism for connecting either a trial or final prosthetic element to the device, the mechanism including a plurality of fasteners for:

a) adjusting the positioning of the prosthetic element in one or more dimension, b) rigidly locking the prosthetic element into place upon achieving a desired orientation, c) temporarily disconnecting the prosthetic element from the mechanism for cement injection, d) reconnecting the prosthetic element to the mechanism in the desired orientation for cement curing and fixation, and e) removing the mechanism 16. The method of claim 12, wherein the prosthetic element is a final prosthetic element, the method further including the steps of:

cementing the prosthetic element into position once the desired orientation is achieved; and removing the structural assembly.

17. The method of claim 12, further including the steps of:

temporarily removing the prosthetic element once the desired orientation is achieved;

returning the prosthetic element into the desired orientation for fixation; and removing the structural assembly.

18. The apparatus of claim 1, wherein the prosthetic element is associated with knee-replacement surgery.

19. The apparatus of claim 1, wherein the prosthetic element is associated with shoulder arthroplasty.

20. The method of claim 17, wherein:

the prosthetic element temporarily removed for the application of cement is a trial prosthetic element; and the prosthetic element returned to the desired orientation for fixation is a final prosthetic element.

21. The method of claim 12, wherein the prosthetic element is associated with knee-replacement surgery.

22. The method of claim 12, wherein the prosthetic element is associated with shoulder arosthroplasty.

23. The apparatus of claim 1, wherein the bone is a humerus and the prosthetic element is an intramedullary trial or final implant.

24. The apparatus of claim 5, wherein the connection between the first and second structural elements may be loosened to permit the prosthetic element to be removed, with the second structural element rigidly attached thereto, such that the element may be returned to the same desired orientation.

* * * * *